(12) United States Patent
Kawai et al.

(10) Patent No.: US 6,458,944 B1
(45) Date of Patent: Oct. 1, 2002

(54) HUMAN BMP-4 PROMOTER AND METHOD FOR EXPLORING BONE-RELATED SUBSTANCE BY USING THE SAME

(75) Inventors: Shinji Kawai, Paris (FR); Takeyuki Sugiura, Tokyo (JP)

(73) Assignee: Aventis Pharma S.A., FRX ( * ) Notice: Subject to any disclaimer, the term of this patent is extended or adjusted under 35 U.S.C. 154(b) by 0 days.

(21) Appl. No.: 09/674,460

(22) PCT Filed: Apr. 22, 1999

(86) PCT No.: PCT/IB99/00732

§ 371 (c)(1), (2), (4) Date: Nov. 30, 2000

(87) PCT Pub. No.: WO99/57145

PCT Pub. Date: Nov. 11, 1999

(30) Foreign Application Priority Data

Apr. 30, 1998 (JP) ............................................. 10-120173

(51) Int. Cl.[7] .......................... C07H 21/04; C12Q 1/68; C12P 19/34; C12N 15/85; C12N 15/86

(52) U.S. Cl. .................. 536/23.5; 536/23.1; 536/24.33; 435/6; 435/91.1; 435/91.2; 435/243; 435/320.1; 435/325; 435/410

(58) Field of Search .......................... 435/6, 243, 320.1, 435/325, 410; 536/24.1

(56) References Cited

FOREIGN PATENT DOCUMENTS

| WO | 9638590 | 12/1996 |
| WO | 9823740 | 6/1998 |

OTHER PUBLICATIONS

Wozney et al. GenBank Accession No.: I62859.*
XP002062064 pp. 789–793 Genomic . . . Multiple Transcripts.
XP002121984 pp. 559–560 Finge Mapping . . . Hybridization.
XP002029032 pp. 1049–1056, Murine Bone . . . Region vol. 192, No. 3, 1993.
XP002029031 pp. 28364–28373 The Mouse . . . Gene, vol. 270, No. 47 1995.
XP002120993 pp., 221–229 The Human . . . Regulation 1998, Shore et al.

* cited by examiner

*Primary Examiner*—Gary Benzion
*Assistant Examiner*—Alexander H. Spiegler
(74) *Attorney, Agent, or Firm*—Bierman, Muserlian and Lucas

(57) ABSTRACT

The present invention provides a method for exploring low molecular weight compounds which regulate positively or negatively the expression of human BMP-4 with reference to a reporter activity by using 5' upstream region gene containing the human BMP-4 promoter and an animal cell introduced with a recombinant expression vector that has been connected to an appropriate reporter gene. The low molecular weight compounds and their derivatives obtained by the present method have morphogenetic activity and inhibiting activity for bone and cartilage through the expression of human BMP-4 and are useful as preventive or therapeutic agents for cartilage and bone diseases.

6 Claims, 5 Drawing Sheets

HUMAN BMP-4 PROMOTER AND METHOD FOR EXPLORING BONE-RELATED SUBSTANCE BY USING THE SAME

This application is a 371 of PCT/IB99/00732 filed Apr. 22, 1999.

BACKGROUND OF THE INVENTION (1) Field of the Invention

The present invention relates to a 5' upstream region DNA containing a promoter of a human bone morphogenetic protein (BMP, hereafter-4). Further, the present invention relates to a method for exploring a low molecular weight compound positively or negatively which regulates the expression of human BMP-4 by using a mass of animal or yeast cells that are introduced with a 5' upstream region DNA containing the human BMP-4 promoter and a recombinant expression vector integrated into a suitable reporter gene, and by using a reporter activity as an indicator.

(2) Description of the Related Art

At present, a bone morphogenetic activity has been reported for a bone morphogenetic factor, BMP, belonging to TGF (transforming growth factor) -β superfamily (Science 150, 893–897, 1965; Science 242: 1528–1534, 1988). Known species of BMP are BMP-1 to BMP-14. Among them, the members from BMP-2 to BMP-14 have been known as showing the bone morphogenetic activity. BMPs ranging from BMP-2 to BMP-14 are considered as effective to therapeutic and preventive treatment for various bone dysfunction and bone diseases, however, they exist in very small amount in nature. Therefore, an available large quantity from BMP-2 to BMP-14 used for these treatments requires production of recombinant protein. The production of the recombinant protein generally is very expensive compared with a low molecular weight compound. On the other hand, there are many restrictions as a medical drug in terms of physical properties and administration due to its proteinic characteristics. Considering these points, a small molecular organic compound having the equal activity to that of said BMP protein, if any, will become a very promising medical drug. The substance obtained by the exploring method provided by the present invention has the activity to induce the expression of human BMP-4, a bone morphogenetic protein, and also has the same activity as that of human BMP-4 to be a very useful application. On the contrary, there is a report (New Engi. J. Med., Vol. 335, p. 555–561, 1996) suggesting that human BMP-4 causes bone and cartilage hyperplasia. In this case, inhibiting the expression of human BMP-4 may prevent osteohyperplasia. The present invention is able to detect the inhibition of the expression of human BMP-4 and provides a method for exploring a substance which prevents such hyperplasia.

For such an exploring method, an example was so far only reported using a murine BMP-2 promoter (WO97/15308); there is no example of using a human BMP-4 promoter. The region of the murine BMP-4 promoter has been already cloned (Biochem. Biophys. Acta, Vol. 1218, p. 221–224, 1994), but no detailed sequence data of the human BMP-4 promoter has been elucidated. The present invention first disclosed the sequence of the human BMP-4 promoter. The homology of the entire sequence of 5' upstream region DNA between human and murine BMP-4 (J. Biol. Chem., Vol. 270, p. 28364–28373, 1995) is 52.2%. The materials for the exploring method provided by the present invention are all derived from human sources so that the substance obtained by the exploration would be a clinical application practically. It is expected to obtain a substance capable of more accurate regulation of the human BMP-4 expression by transfecting two promoters (promoter 1 and promoter 2) separately or simultaneously in the recombinant expression vector into the host cells.

SUMMARY OF THE INVENTION

The present invention provides a 5' upstream region DNA containing a promoter of human BMP-4. By using 5' upstream region gene containing the human BMP-4 promoter and an animal cell introduced with a recombinant expression vector which has been integrated in an appropriate reporter gene, the low molecular weight compounds which regulate positively or negatively the expression of human BMP-4 can be explored with reference to a reporter activity. The low molecular weight compounds and their derivatives have morphogenetic activity and inhibiting activity for bone and cartilage through the expression of human BMP-4 and are useful as preventive or therapeutic agents for cartilage and bone diseases, remedies for osteometastasis, or therapeutic and preventive agents for osteohyperplasia.

DESCRIPTION OF THE PREFERRED EMBODIMENT

Figure 1:
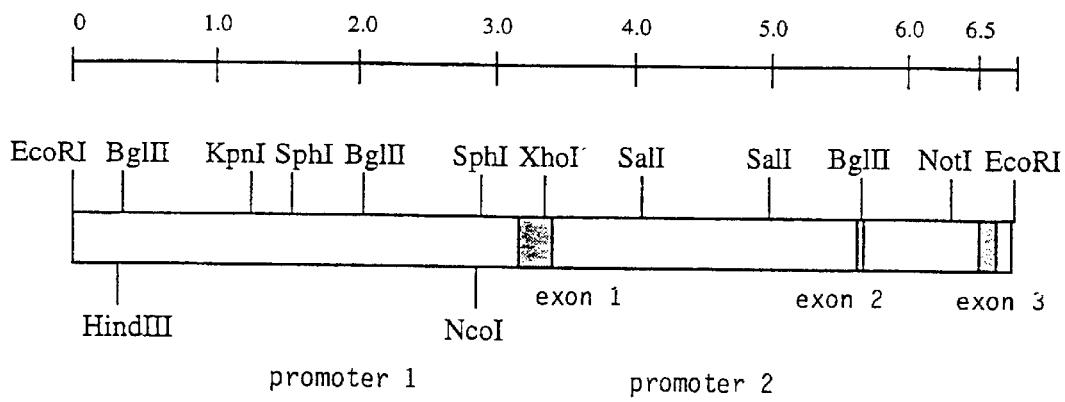
FIG. 1 is an exon-intron structure of 6.7 kb 5' upstream region of human BMP-4 gene and a restriction enzyme map.

The present invention relates to a DNA whose nucleotide sequence is represented by the base sequence No. from 1 to 6774 in SEQ ID NO. 1 of the Sequence Listing that encodes a human bone morphogenetic protein-4 promoter region, or a fragment thereof. SEQ ID NO. 1 of the Sequence Listing shows the 5' upstream region sequence of the human BMP-4 gene.

The present invention relates to a method for preparing the DNA shown in SEQ ID NO. 1 of the Sequence Listing by conducting the steps of:

(1) digestion of a human placenta genomic DNA with a EcoRI restriction enzyme, (2) isolation by agarose gel electrophoresis, (3) cloning of the isolated DNA fragment digested with EcoRI into a lambda phage vector λDASH II treated with the same enzyme, (4) packaging of said vector into the phage,
(5) establishment of genomic DNA library by infecting Escherichia coli with the phage,
(6) screening by PCR, and
(7) subcloning into a plasmid vector.

The plasmid vector used herewith is not restricted and can be used among ones commercialized. A pUC18 vector can be a preferable example.

The present invention relates to a recombinant expression vector characterized by integration of the full length or a part of DNA shown in SEQ ID NO. 1 of the Sequence Listing into a reporter gene. In detail, the recombinant expression vector is constructed by locating a suitable region of 5' upstream region of the human BMP-4 gene which is represented by SEQ ID NO. 1 of the Sequence Listing in front of a reporter gene. The reporter gene such as luciferase or β-galactosidase gene shows an expressing status on behalf of an original product. The vector as the original for the recombination expression vector is not specially restricted but to allow to use a plasmid vector commercialized. The present invention used pGL3-basic as a preferable example. The use of pGL3-basic yielded pMSS116 (8.2 kb), pMSS118 (7.1 kb), and pMSS119 (10.5 kb) that are the recombination expression vectors containing the human BMP-4 promoter and luciferase reporter genes. The present invention assigned them to the recombination expression vectors. It is necessary to introduce the recombinant expression vector to mammalian cells, preferably human osteoblast-like cells, such as SaOS-2 cells, with a liposome. The animal cells stably transfected with the recombinant expression vectors are selected by using a resistance marker.

The present invention relates to a method for exploring a bone-related substance, characterized by using the recombinant expression vector characterized by integration of the full length or a part of DNA shown in SEQ ID NO. 1 of the Sequence Listing into a reporter gene. It relates to the method for exploring a bone-related substance wherein the bone-related substance is osteogenesis inducing substance or a bone-related substance wherein a bone-related substance is osteogenesis inhibiting substance. A low molecular weight compound which induces or inhibits the expression of human BMP-4 can be obtained by isolating the promoter which regulates the expression of the gene, by connecting it to a suitable reporter gene and by introducing the gene structure to a suitable mammal cell to make an exploring system. The substance which regulates the expression of human BMP-4 in the exploring system works on the promoter to increase or decrease the expression level of the reporter gene. Therefore, a simple and easy measurement of the reporter activity makes an exploration of the aimed substance possible.

The animal cell transfected with said vectors can be used for a method for screening a chemical compound library by high throughput screening (Nature, Vol. 384, Suppl., p. 14–16, 1996) and exploring an active substance from natural substances. The substance which increases or decreases an activity is searched by treating the cell with a substance for an appropriate time period and thereafter measuring the reporter activity. The substance obtained hereby can regulate the expression by working directly on a transcription factor or indirectly on the human BMP-4 promoter through regulating a signal transduction system. Therefore, these compounds are effective as a therapeutic agent for osteocartilaginous diseases, cancer metastasis to bone, or osteohyperplasia.

The substance obtained by the present invention has bone or cartilage morphogenetic activity and is effective as an agent for therapeutic and preventive treatment in the fields of orthopedic surgery (fracture, osteoarthritis such as joint osteoarthritis and hip joint osteoarthritis, arthrosteitis, damage of cartilage such as damage of meniscus, regeneration of bone and cartilage deficit caused by injury and tumor dissection, bone reconstruction such as spinal fusion and vertebral canal enlargement, and congenital cartilage and bone diseases such as dysoteogenesis and achondroplasia), or dental fields (bone reconstruction such as palatoschisis, mandible reconstruction, and residual ridge construction), and osteoporosis. Moreover, the substance of the present invention can be used for bone graft in aesthetic surgery. These therapeutic treatments are effective to therapies in the fields of veterinary surgery. On the other hand, the present invention can provide a substance to inhibit bone or cartilage morphogenesis. In this case, the substance is applied as an agent for prevention and therapy of bone and cartilage hyperplasia.

EXAMPLES

This invention shall be more illustratively explained by way of the following Examples. The following Examples are to be considered in all respects as illustrative and not restrictive.

Example 1

Isolation of 5' Upstream Region of Human BMP-4 Gene

A human placenta genomic DNA (a product of CloneTech) was digested by using various kinds of restriction enzymes (BamHI, BglII, EcoRI, HindIII, PstI, SacI, SalI, SmaI, SphI, and XbaI), separated by agarose gel electrophoresis, transferred to a nylon membrane, and subjected to the Southern hybridization under a standard condition using BMP-4 cDNA (Science 242, 1528–1534, 1988) as a probe. As the result, it was found that digestion by the restriction enzyme EcoRI among restriction enzymes used yielded a DNA fragment of ca. 7 kb containing the longest human BMP-4 gene. Then, a human placenta genome DNA was digested by the restriction enzyme EcoRI and separated by agarose gel electrophoresis to extract a DNA fragment of ca. 7 kb from the agarose gel. The DNA fragment obtained was cloned to a lambda phage vector λDASH II (Stratagene Ltd.) digested by the restriction enzyme EcoRI. The vector was in vitro packaged by Gigapack III XL Extract (Stratagene Ltd.), infected to *Escherichia coli* XL1-Blue MRA (Stratagene Ltd.) to make a genomic DNA library. The library was divided into pools. Each pool was amplified by a screening (Nucleic Acids Research 21: 2627–2631, 1993) using PCR; namely, the PCR method by using PCR primers (SEQ ID NO. 2 and SEQ ID NO. 3 of the Sequence Listing) corresponding to the exon 1 region to select the objective pool, to yield finally 5' upstream region (6.8 kb) of human BMP-4 gene. In addition, the 5' upstream 6.8 kb fragment was subcloned to a pUC18 vector (a product of Amersham Pharmacia Biotech). The vector was named *E. coli* pKOT 312. The *E. coli* pKOT 312 was deposited in National Institute of Bioscience and Human-Technology, Agency of Industrial Science and Technology, Ministry of International Trade and Industry 1-3, Higashi 1-chome, Tsukuba-shi Ibaraki-ken 305–8566 Japan, in Mar. 30, 1998 with depositary number FERM P-16736 and transferred to the International Depository Authority under Budapest Treaty on Feb. 17, 1999 (Deposit No. FERM BP-6650).

Example 2

Determination of DNA Sequence of 5' Upstream Region of Human BMP-4 Gene

The sequence of 5' upstream region of human BMP-4 gene obtained was determined by Amersham Pharmacia Biotech's ALF DNA Sequencer according to the method of Sanger et al. (Proc. Natl Acad. Sci. USA 74: 5463–5467, 1977). The sequence thus analyzed is described in SEQ ID NO. 1 of the Sequence Listing.

Example 3

Figure 2:
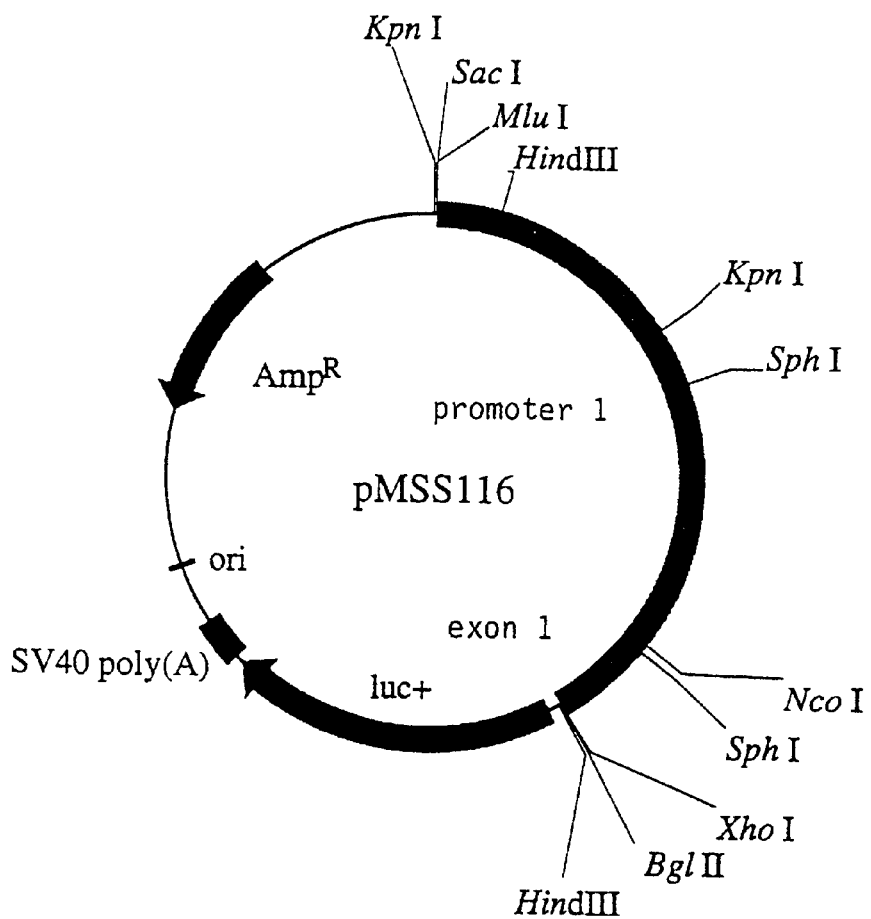
FIG. 2 is a recombinant expression vector (pMSS116) containing the promoter 1 of 5' upstream region of human BMP-4 gene. The promoter 1 region (base No. from 1 to 3361 shown in SEQ ID NO. 1 of the Sequence Listings, from 5' terminal to XhoI shown in FIG. 1) was inserted to the NheI and XhoI restriction enzyme site of pGL3-basic.
Figure 3:
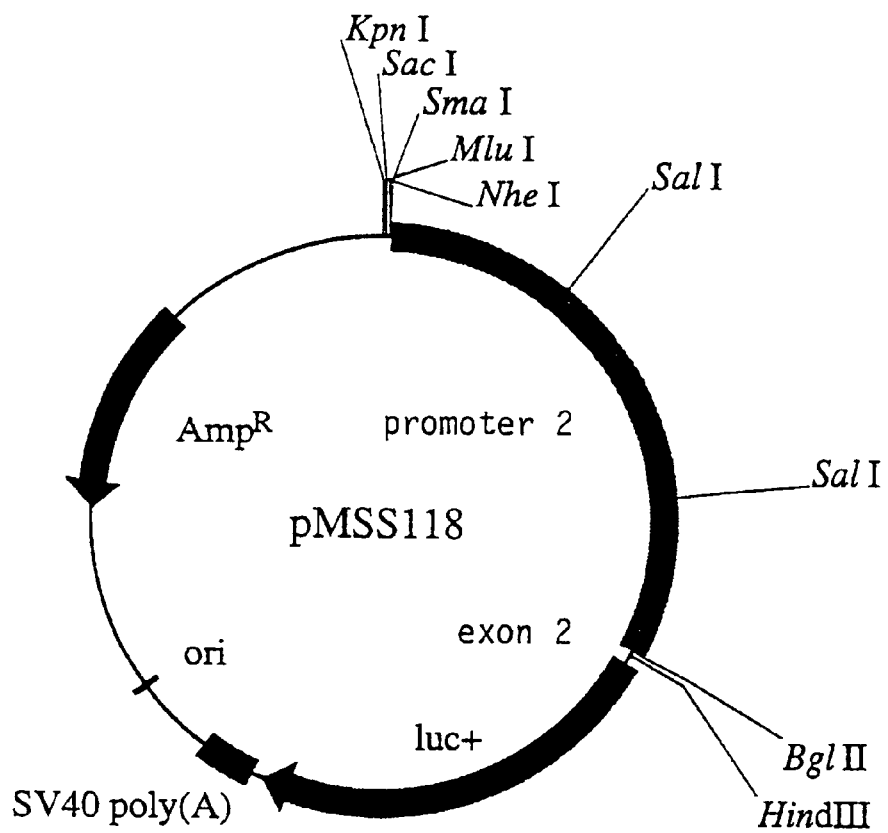
FIG. 3 is a recombinant expression vector (pMSS118) containing the promoter 2 of 5' upstream region of human BMP-4 gene. The promoter 2 region (2.3 kb) (base No. from 3361 to 5645 shown in SEQ ID NO. 1 of the Sequence Listings, from XhoI to BglII of exon 2 shown in FIG. 1) was inserted to the XhoI and BglII restriction enzyme site of pGL3-basic.
Figure 4:
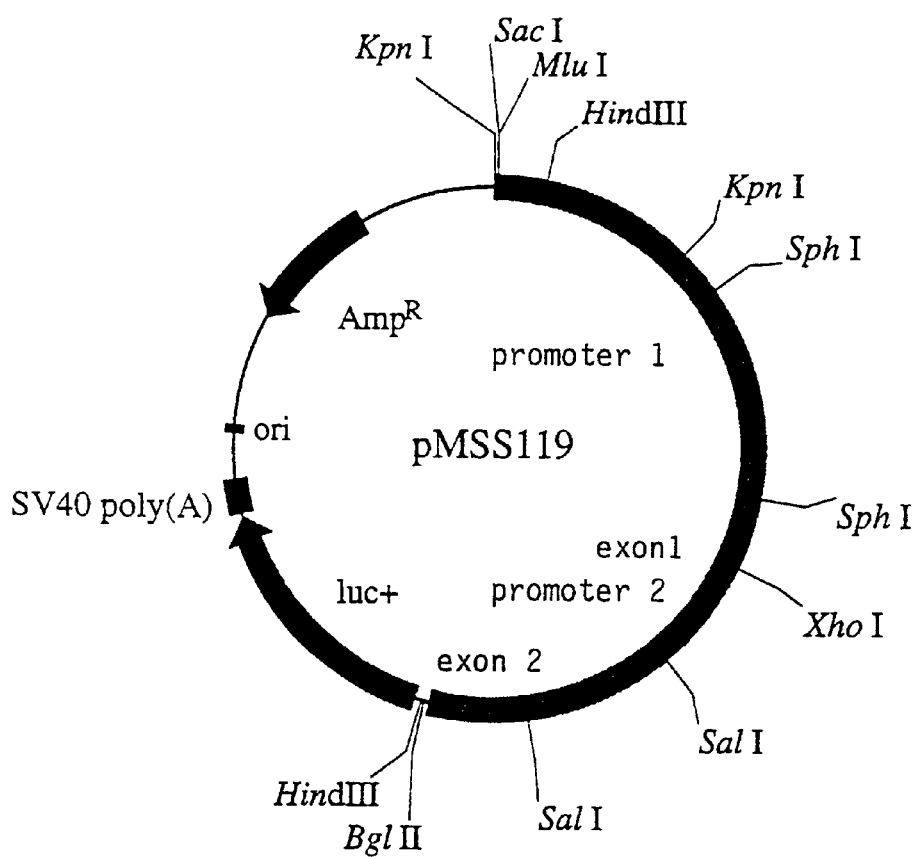
FIG. 4 is a recombinant expression vector (pMSS119) containing the promoter 1 and the promoter 2 of 5' upstream region of human BMP-4 gene. The promoter 1 and the promoter 2 region (base No. from 1 to 5645 shown in SEQ ID NO. 1 of the Sequence Listings, from 5' terminal to BglII of exon 2 shown in FIG. 1) were inserted to the NheI and BglII restriction enzyme site of pGL3-basic.

Construction of a Recombinant Expression Vector Containing The Human BMP-4 Promoter and a Luciferase Reporter Gene As shown in FIG. 1, human BMP-4 has two promoters before exon 1 (promoter 1) and after exon 2 (promoter 2) similar to the promoter structure of mouse BMP-4. Then, a region containing the promoter 1 (from 5' terminal to Xho1 described in the FIG. 1) was inserted into the upstream restriction enzyme sites, NheI and XhoI, of the reporter gene of a luciferase reporter vector pGL3-basic (a product of Pro Mega Ltd.) by using XbaI restriction enzyme site derived from the pUC18 vector existing in the 5' terminal to construct a recombinant expression vector pMSS116 (8.2 kb). This is shown in FIG. 2. Further, a recombinant expression vector pMSS118 (7.1 kb) was obtained by inserting a region (from Xho1 to BglII in exon 2 described in FIG. 1) containing the promoter 2 into the restriction enzyme sites, XhoI and BglII, of pGL3-basic. This is shown in FIG. 3. Furthermore, a region (from 5' terminal to BglII in exon 2 described in FIG. 1) containing both the promoter 1 and the promoter 2 was inserted into the restriction enzyme sites, NheI and BglII, of pGL3-basic by using XbaI site derived from the pUC18 vector, as in the case of pMSS116 to construct a recombinant expression vector pMSS119 (10.5 kb). This is shown in FIG. 4.

Example 4

Measurement of the Activity of the Human BMP-4 Promoter (Introduction of a Recombinant Expression Vector to a Human Cell and Transient Expression)

Figure 5:
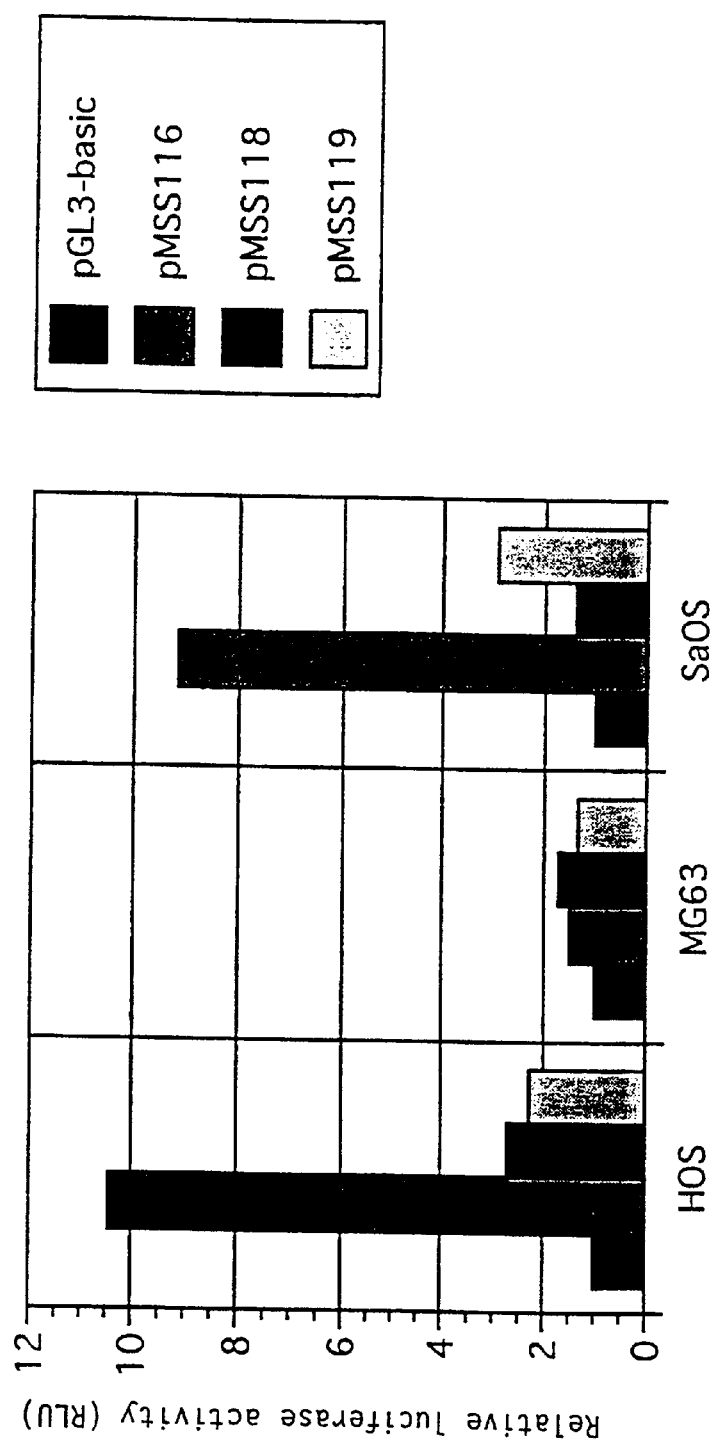
FIG. 5 is a result of measuring a human BMP-4 promoter activity (transiently expression).

In order to express transiently the human BMP-4 recombinant expression vector, above-described recombinant expression vectors (pMSS116, pMSS118, pMSS119) were mixed with a vector, pRL-SV40 (a product of Pro Mega Co.) containing sea pansy luciferase gene as an internal control for measurement of efficiency of gene introduction in equal quantity. Then, cationic liposome lipofectamine (a product of Lifetech Oriental Co.) was mixed with said DNA solution to add to human osteosarcoma cells HOS, MG63, and SaOS-2 for transfection. Fire fly luciferase activity and sea pansy luciferase activity were measured by Pikka Gene Dual Kit (a product of Toyo Ink Co.). The result is shown in FIG. 5. The promoter activity was expressed as a ratio of fire fly luciferase activity to sea pansy luciferase activity. From the result, it has been known that the DNA of SEQ ID NO. 1 of the Sequence Listing has a promoter activity.

Example 5

Introduction of the Human BMP-4 Recombinant Expression Vector to a Human Cell and Stabilized Expression In order to express the human BMP-4 recombinant expression vector stably, above-described vectors were mixed with a vector pPUR (a product of CloneTech Ltd.) containing puromycin resistant gene in the proportion of 10:1 and also mixed with cationic liposome lipofectamine (a product of Lifetech Oriental Co.) to add to a human osteosarcoma cell HOS for transfection. The cells to which the aimed gene has been introduced were selected from a culture medium containing puromycin (a product of Sigma Ltd.).

Example 6

Screening of Active Low Molecular Weight Compound

Cells selected were inoculated in a 96-well plate, treated with substances of various chemical compound libraries for 1–3 days, dissolved with a cytolytic agent (a product of Pro Mega Ltd.), and measured for enzyme activity by employing a luciferase assay kit (a product of Pro Mega Ltd.). By such processes, various substances inducing or inhibiting the expression of human BMP-4 can be explored.

---

What is claimed is:

1. An isolated nucleic acid of SEQ ID No: 1 that encodes a human bone morphogenetic protein-4 promoter region.

2. A method for preparing an isolated nucleic acid of SEQ ID No: 1 comprising the steps of:
 (1) digesting a human placenta genomic DNA with a EcoRI restriction enzyme to form a mixture,
 (2) subjecting the digestion mixture to agarose gel electrophoresis to isolate a DNA fragment,
 (3) cloning the isolated DNA fragment digested with EcoRI into a lambda phage vector λDASH II treated with the same enzyme,
 (4) packing of said vector into the phage,
 (5) establishing a genomic DNA library by infecting *Escherichia coli* with the phage,
 (6) screening by PCR, and
 (7) subcloning the 5' upstream of human BMP-4 gene into a plasmid vector to obtain the derived isolated nucleic acid.

3. A recombinant expression vector wherein the full length of the isolated nucleic acid of SEQ ID No: 1 is integrated into a reporter gene.

4. A method for exploring for a bone-related substance, comprising introducing the recombinant expression vector of claim 3 to determine the pressure of the bone-related substance.

5. The method for exploring a bone-related substance of claim 4, wherein the bone-related substance is an osteogenesis inducing substance.

6. The method for exploring for a bone-related substance of claim 4, wherein the bone-related substance is an osteogenesis inhibiting substance.

* * * * *

SEQUENCE LISTING

```
<160> NUMBER OF SEQ ID NOS:  3

<210> SEQ ID NO 1
<211> LENGTH: 6774
<212> TYPE: DNA
<213> ORGANISM: HUMAN
<220> FEATURE:
<221> NAME/KEY: misc_feature
<222> LOCATION: (1)..(6774)
<223> OTHER INFORMATION: Human BMP-4  5' upstream gene sequence
      including the exon 1 through exon 3 regions.

<400> SEQUENCE: 1
gaattccttc cgtagcttca ccagacacct aattggccaa gaaggtttga agacctgatg       60
tggttcttaa ttggggatgg ggaattaagg gctactgtat ctataggatt atcttttcac      120
ttgcatagac ctatttggtg tgttcagggc atagtgatac tataattgcc atatttaaca      180
gtttataaag ttcaagccca gcatattctt tgcctgttta atgatgtctt ggtatcagcc      240 tttttaatggt acttatcagc atagaaaatg gaaacaaaat aacttttaaa acagtagctc      300
```

-continued

```
tcaagcttta gtgtgctcag aatgaccaga gaaccttgtg aaatatacag atttctgggt      360
ccagatctgg ggcaggacca ggaagtctgc atttcatctg cacccccacc ctactctgag      420
gcttatagtc ctgagaacat gctttgaaaa aggctgtccc aagggctcgc agacaggcta      480
ttgaccagct actctttctt gatgttctcc aggaaaaccc aacaaaggaa tgcctttcat      540
tgagtagtag cagcatagga gcaatagttg ctcctgaatt atgggtgggt ttccctcttc      600
atcaatgtgc tttaagggta cagtttcatt tggtctatct accatgttct ataaaaacat      660
gaaaattcac aggtaagttt gagatacaga aaataactaa actgattctt ctcacgaact      720
ctgatcacta ggctgtggtt gatttagctc tctaaccaac aagtaatttg ttctttggca      780
tgagtaaggg gggaaaagga ggagtgggta aaagcagctg ataacagatg gcttgcgccc      840
atctaaaatg tggggagaga aataaagctg tcccaagaga actaaagctg agttctctcg      900
tcatatatct gaagattcat atcagggggtc taaacatggt atgtcgggta gcttaattgg      960
aaactcctgg actgtgagtg tcacagactc atggatgggc caatcagtgg ccactttagt     1020
gtctgggctg cagcaaaatg agacaatagc tgtcattcaa aaacctttgg aattaaaaaa     1080
accccgaaat gacattggtg ctttaaagta aaataaagtc ctgcctttaa gtccagcata     1140
tcactgttgt ttctgagttt aaatattaag aaccacattt cgttaatgat taaaacaaca     1200
gtgattgatt taggggctca gtgagcattt aatctgtcct gacttcaggt accatgctaa     1260
aggagcacaa tgcctgatgc tgcaggagaa acattaggta actatttaat ggagttttaa     1320
ttttctgtta ttatttttaa taattaattg tgattttgac tatttggaag ctacaggtat     1380
attttgtcct ccttttgggg tggtgttatt gccctgccct gttttaatca gtggttctta     1440
gagaaagtga actcaggagt gacttaaaat gaaggaagac ggactttggc taaaattaca     1500
attaaataat caaatcattt tcaaatataa agggagcatg cagatgatct ggcccaatcc     1560
tttcattctg cagatgagaa aactgaggct cataggaatg aaaagacttg cccaaagcca     1620
tacagcttgt ttctgttgtt tggtgcatta ggccaaaaga cctaggccta atagatggaa     1680
aatatggcag gatgtcttgg ccttgctctg acagttgctt ctctgatctc agatatttcc     1740 cacccttgt aaattctgtg ttccacacag gaagtagttc ttgtttttta aatatcgaag     1800
gtgtataaac gtaaagtttt tatagatgag ccacccaggg ccaatatctg tttaagtaaa     1860
gacctaaatg ctttgcagag acagtaaagt gtcatgtctg tcccagggaa agaaatccag     1920
gacaggaaat gctcagtctt ccagcactcc tctggctacc tggagctcag gctatgagcc     1980
tcaacccctc cctgaagcat agctctggga gcagaggctg tgatttactt cagagatctg     2040
ggcaagtccc tttaacctgg tagtccttcc tttccttgtt tgtaaaacag agagatgagg     2100
ctgatagctc cctcacagct ccatcagagg cagtgtgtga aattagttcc tgtttgggaa     2160
ggtttaaaag ccaccacatt ccacctccct gctaatatga ttactaaaat gttttatat     2220 gaaagggcca attcctcatc tccctcttc ctttaaaaac agaccaaggg gcatcttttc     2280
ttgtctccct gtggcctaaa aggttactgc ttctgtggtt atctccttgg aaagacagag     2340
tgtcaggact cttaggtaca ccaaaaatga acaaaaaaat caacaacaac cataacacca     2400
acaaaaataa ctgctgtgtc ggttcttaag acggcttctg agctagaaac agattttttct    2460 aactgtaaaa aacgtggccc cagcctgtct gcaggccacc tctgtcttta ggccttgggg     2520
ggaggaggga agtgagctca tttactgggt ctacctcagg gtcatcacca aggtgttcta     2580
caaaacgcac tttaagaatg ttttggaagg aaattcacct tttaacagcc caagaggtat     2640
```

-continued

```
ctctctctgg cacacagttc tgcacacagc ctgtttctca acgtttggaa atctttaac      2700 agtttatgga aggccacctt ttaaaccgat ccaacagctc ctttctccat accctgattt     2760
tagaggtgtt tcattatctc taattactca gggtaaatgg tgattactca gtgttttaat    2820
catcagtttg ggcagcagtt acactaaact cagggaagcc cagactccca tgggtatttt    2880
tggaaggtac ggcgactagt cggtgcatgc tttctagtac ctccgcacgt ggtccccagg    2940
tgagccccag ccgcttccca gagctggagg cagcggcgtc ccagctccga cggcagctgc    3000
ggactcggcg ctgcctgggc ttccgggacc cgggcctgct aggcgaggtc gggcggctgg    3060
aggggaggat gtgggcgggg ctcccatccc cagaaaggga ggcgagcgag ggaggaggga    3120
aggagggagg ggccgccggg gaagaggagg aggaaggaaa gaaagaaagc gagggaggga    3180
aagaggagga aggaagatgc gagaaggcag aggaggaggg agggagggaa ggagcgcgga    3240
gcccggcccg gaagctaggt gagtgtggca tccgagctga gggacgcgag cctgagacgc    3300
cgctgctgct ccggctgagt atctagcttg tctccccgat gggattcccg tccaagctat    3360
ctcgagcctg cagcgccaca gtccccggcc ctcgcccagg ttcactgcaa ccgttcagag    3420
gtccccagga gctgctgctg gcgagcccgc tactgcaggg acctatggtg agcaaggcta    3480
cctggtgagg ggagacaggc agaggggtc taggagcctc cttgggggga agaagctggt     3540
cacaggctgt gaccgaggca aaggtggcc taattatttt ccaatagtgg tgctggaggt     3600
ggggatgctg gcgctgaaag acctttaaat atcggctact gccctgccca ggccttctct    3660
gtccagcagt ccctgggaga gtctcacctt tgggaagtgc ggggcaggag agcagaaaca    3720
agagaagccc ttggtagggg ggtcgttggg aaaaactgtg gggtcttggg ctgaacgcgt    3780
tgcccacggg ctggaggttg cgatccccgg acggaaagcg cggggaggag aaggagagaa    3840
ccggctctga ggtccagaga gagtgagggg gcagagcgac ggcgagatgg ggagagaaca    3900
cctagctgga gcaggttctg cggtagagag cgcagtcctg ctggcctctg gagagtgcgc    3960
gccgctccgg aggctgcgtc gagggagtg tcacccaatc tgggcccag ctggcggggc      4020 gcctgagagc ttgcgaactg cagttgcagg acgcgccttc tccacgagct attttcgtcg    4080
acttgcggaa cccaaggaac ctcgcctcta tcatttcacg gtgtagggtc cctagagacg    4140
acagccaaga tcccaggggc tcccaggacg cttgttcctg cggtgtcgtg tcctatgggg    4200
agttcctggc gggacgaaag gcggacgcgc ggctcttcct ggccctccag gcccggaacc    4260
gacgggaaag gttcccgtga ttcccgagtc cctgcaggct tcttccagcg ggagttggtc    4320
cgggggcctt agacgcctcc aagcactgct ttggaggatg gtttccaagg atcgcggttt    4380
gtgagttgaa ggctttgtga gaggttaaac ccccaaaaga tacatacttg gtaaactgag    4440
gctacctgta aacacatttc ggcattagga gaagattcga gtagggaagt gaaggacaac    4500
caccccgagt tacattcctt tcccccaata aaaagctctg gggatgaaag ttcttttggc    4560
ttttatcttt tcgatttaaa aatttgagaa gaaatgtga ctagagatga atcctggtga     4620
atccgaaatt gaaacacaac tcccccttcc ccttcctatc ctctcggttt tagaaccgcg    4680
ctctcccgcc ccaggagatt ccttggggcc gagggttttc cggggaaccg ggcgcccgcc    4740
ccttctactg tcccttttgcc ccgcgggcac agcttgcctc cgtctgcttt ctctacttct   4800
ggacctctcc tcggcgggct ttttaagggg cttctgcgtc tcaaaacaaa acaaaaaaac    4860
cctttgctct tcccaaccct ttcgcagccc gccccagcgt ggcgcgggac cagcaaaggc    4920
gaaagcgccg cggctcttgc cgggcgcgga cggtcgcgca gggcgcccg cggcctccgc     4980 acccggacct gaggtgttgg tcgactccgg gcatccacgg tcgggaggga gggctgagct    5040
```

```
gttcgatcct ttacttttct tcctcaaagt ctacctgcca atgcccctaa gaagaaaacc    5100
aagtatgtgc gtggagagtg gggcggcagg caacccgagt tcttgagctc cggagcgacc    5160
caaagcagca actgggaaca gcctcaggaa agggaggtcg ggtggagtgg gctttggggc    5220
aggagtcatg gggcccgggc cccggggacg acctggcgct cccggccctg ctgaacgctg    5280
agttgcgcct agtcgggttt tcgaagaggc ccttgcgcag agcgacccac gcgcgcggca    5340
gcatcttcga ttagtcagga catcccagta actgcttgaa ctgtaggtag gtaaaattct    5400
tgaaggagta tttgctgcgt gcgactctgc tgctggtgca acgaggaag ggggtggggg    5460 aaggaagtgg cgggggaagg actgtggtgg tggtttaaaa aataagggaa gccgaggcga    5520
gagagacgca gacgcagagg tcgagcgcag gccgaaagct gttcaccgtt ttctcgactc    5580
cggggaacat ggtgggattt cctttctgcg ccgggtcggg agttgtaaaa cctcggccac    5640
attaagatct gaaaactgtg atgcgtcctt tctgcagcga cgcctctttc tgaatctgcc    5700
cggagcttcg agccccggcg tctgtccctc agcctggcat ggcttcttcg ggggtctgct    5760
ttgcatgggg agaggggcca cgcagcggcg gactaggttt ggggattctc ggtaatggac    5820
ccggagcaat gactaacagc cgctccctct cactttccca cagcgatcac cctctaacac    5880
cctccctccc attcccggcc ccgcgcgtga caaggtcggc tgctttcagc cgggagctag    5940
atcggtggcc cggctcttcg gaccttagcg agcgttcgcc aagggtgac tggctgtcat    6000 tgggagcaat atttggcctt gaggagaccc tggggaggaa gtggcgggga gctcgtgttt    6060
gcttgtgtgt gtgtgggggg gtagtgtgtg taacacgcgc gtgggcaggg tccctctgcg    6120 ctttccttt taagtgcctc tcggtggtga ggctttgggc gggtgagact ttcccgacct    6180
cgctcccggc cccacttaag ccgggttcga gctgggagac gcagtccctt cagtgcgccc    6240
caaatcctct ggcttcaggt ggcccggcgc ggggcccag cacgacgcac cgcgccgaga    6300
accgggttct ccggtgcgtg cgccagtagc cctgggagcg cggcggccgc ggggcaccgg    6360
ccgaggctct gccgagcgcc gccgggagct cctcccggac cgctgaggct cgggcggcgg    6420
acgcggaggt tggcctcgcc tggaggggcg ggcccgcgag gggcggggg ctgtggagga    6480 ggggagggcg cgcaggccct ttcgccgcct gccgcgggag gggcctcggc gctcacgtga    6540
ctccgagggg ctggaagaaa aacagagcct gtctgcggtg gagtctcatt atattcaaat    6600
attcctttta ggagccattc cgtagtgcca tcccgagcaa cgcactgctg cagcttccct    6660
gagcctttcc agcaagtttg ttcaagattg gctgtcaaga atcatggact gttattatat    6720
gccttgtttt ctgtcagtga gtagacacct cttccttccc cctccccgga attc    6774
```

<210> SEQ ID NO 2
<211> LENGTH: 30
<212> TYPE: DNA
<213> ORGANISM: HUMAN
<220> FEATURE:
<221> NAME/KEY: misc_feature
<222> LOCATION: (1)..(30)
<223> OTHER INFORMATION: Sense PCR primer for cloning 5' upstream human
      BMP-4 gene sequence corresponding to the exon 1
      region

<400> SEQUENCE: 2
ggcagaggag gagggaggga gggaaggagc                                       30

<210> SEQ ID NO 3
<211> LENGTH: 30
<212> TYPE: DNA

-continued

```
<213> ORGANISM: HUMAN
<220> FEATURE:
<221> NAME/KEY: misc_feature
<222> LOCATION: Complement((1)..(30))
<223> OTHER INFORMATION: Reverse PCR primer for cloning 5' upstream
      human BMP-4 gene sequence corresponding to the exon 1 region

<400> SEQUENCE: 3
gggacctctg aacggttgca gtgaacctgg                                          30
```

Sequence Listing Free Text

<210>1
<223>Human BMP-4 5' upstream gene sequence including the exon 1 through exon 3 regions.
<210>2
<223>Sense PCR primer for cloning 5' upstream human BMP-4 gene sequence corresponding to the exon 1 region.
<210>3
<223>Reverse PCR primer for cloning 5' upstream human BMP-4 gene sequence corresponding to the exon 1 region.